(12) United States Patent
Yang et al.

(10) Patent No.: US 7,635,951 B2
(45) Date of Patent: Dec. 22, 2009

(54) ULTRAVIOLET LAMP

(75) Inventors: Shi Guang Yang, Shanghai (CN); Jian Cheng Wang, Shanghai (CN); Wai Man Chan, Shau Kei Wan (HK)

(73) Assignee: Fabutech Development Co. Ltd., Wanchai (HK)

( * ) Notice: Subject to any disclaimer, the term of this patent is extended or adjusted under 35 U.S.C. 154(b) by 476 days.

(21) Appl. No.: 11/535,952

(22) Filed: Sep. 27, 2006

(65) Prior Publication Data

US 2007/0069654 A1    Mar. 29, 2007

(30) Foreign Application Priority Data

Sep. 28, 2005    (CN) ............... 2005 2 0045379 U

(51) Int. Cl.
*H01J 17/16* (2006.01)

(52) U.S. Cl. ............... 313/635; 313/491; 313/493

(58) Field of Classification Search ............. 313/491, 313/493, 631, 635
See application file for complete search history.

(56) References Cited

U.S. PATENT DOCUMENTS

| | | | | |
|---|---|---|---|---|
| 2,082,963 A | * | 6/1937 | Lorenz | 315/46 |
| 3,128,169 A | * | 4/1964 | Heraeus et al. | 65/111 |
| 4,349,765 A | * | 9/1982 | Brandli | 313/571 |
| 2001/0022499 A1 | * | 9/2001 | Inayoshi | 313/607 |

* cited by examiner

*Primary Examiner*—Vip Patel
(74) *Attorney, Agent, or Firm*—Intellectual Property Law Group LLP; Juneko Jackson; Otto O. Lee

(57) ABSTRACT

The present invention relates to an ultraviolet lamp comprising a glass shell and an electrode fixed on one or more ends of the lamp, where each electrode is a coiled wire with a hollow conical shape. The hollowed conical structure of the electrode reduces the thermal capacity of the electrode as compared with other types of electrodes of the same mass, makes the lamp start quicker, and decreases the emission loss of the electrode when the glow discharge is transformed to an arc discharge. The lamp of the present invention has a wide electrode surface area, such that the loads on each point of the emissive surface are equally distributed, thus decreasing the electron scattering and dispersion, and allowing the lamp to resist the impact from positive ions. Due to the shape and structure of the electrode, the lamp of the present invention has increased efficiency and emitting ability, and allows for a longer lasting lamp.

18 Claims, 1 Drawing Sheet

ULTRAVIOLET LAMP

CROSS-REFERENCE TO RELATED APPLICATIONS

This application claims foreign priority under 35 U.S.C. § 119 to Chinese Patent Application no. 200520045379.4, filed in the People's Republic of China on Sep. 28, 2005, the entire contents of which are hereby incorporated by reference.

BACKGROUND OF THE INVENTION

1. Field of the Invention

The present invention relates to a gas-discharge lamp, in particular an ultraviolet (UV) lamp.

2. Related Art

There are generally two kinds of UV lamps: cold-cathode lamps and hot-cathode lamps. Hot-cathode UV lamps have the disadvantages of being bulky, having short life spans, being unstable, having low radiant intensity, and decreasing in radiant intensity over time because the coating of the filament oxidizes so quickly, evaporates and peels off. Cold-cathode UV lamps have a higher resistance to damage from shaking and longer life spans than hot-cathode UV lamps. Cold-cathode lamps have been used in many types of liquid crystal displays (LCDs), scanners, and other such technologies because of its symmetrical, high intensity radiance and the fact that they can be made into very fine objects of various shapes.

Cold-cathode lamps are very bright and highly efficient. They also consume a lower amount of energy and have a long life span. Furthermore, cold-cathode lamps have good resistance to damage from shaking. Such lamps can restart easily and start even in lower temperatures. Compared to hot-cathode lamps, cold-cathode lamps emit less heat, are smaller in diameter, and can be used as the lighting source for LCD screens.

Conventional cold-cathode UV lamps, as shown in FIG. 1, are comprised of a glass shell 4, an electrode 5 that is set on the end of the lamp, and a fluorescent coating 6 on the inner surface of the glass shell. The emitting ability of prior art lamps is not very good because of the dispersion and scattering of electrons which do not allow for greater brightness. The brightness of the lamp depends on the amount of electric current applied to it; in this way, an increase in temperature affects the life of the lamp. The typical rated life spans of cold-cathode lamps are about 20,000 hrs, but the actual life span is much shorter due to variables such as number of times lamps are switched on and off as well as operating temperature. In addition, since the thermal requirement of the electrode is significant, (i.e. the electrode needs to be heated up enough to vaporize the mercury inside the lamp) the lamp requires some time to start after an electric current is applied.

SUMMARY OF THE INVENTION

The object of the present invention is to provide an UV lamp, which starts more quickly and has increased brightness and lifespan.

In order to solve the technical problems presented by the prior art, an embodiment of the invention comprises a "U" shaped UV lamp comprising a glass shell, and an electrode on each end of the lamp wherein each electrode is coiled and in the shape of a hollow cone.

The lamp is long and thin, which allows the working voltage to be high while the current remains low. This decreases the energy consumption of the electrode and the self-absorption rate of the electric particles during gas discharge. The hollow conical electrode requires less heat than an electrode of the same mass and therefore allows the lamp to start more quickly and decreases the emission loss when the glow discharge is transformed to the arc discharge of the electrode. The surface area of the coiled wire electrode is larger than that of a common wire electrode of similar type. As such, the emission loading is evenly distributed on the emission surface. Unlike common UV lamps, the emission loading is changed from point emission to surface emission, thus decreasing the electron scattering and allowing the lamp to resist the fierce impact from positive ions. The lamp in an embodiment of the present invention is thereby more efficient, brighter, and longer lasting than prior art lamps.

The lamp in an embodiment of the present invention also has an ozone resistant layer covering the outer surface. This layer is made of nano-materials such as nano-$TiO_2$, and while the lamp is on, the concentration of ozone is controlled, and meanwhile it can improve the efficiency of photocatalysis of the UV lamp and can improve its sterilizing ability. This element of an ozone resistant layer can improve the usefulness of the present invention in the photocatalysis field.

These and other embodiments of the present invention are further made apparent, in the remainder of the present document, to those of ordinary skill in the art.

BRIEF DESCRIPTION OF THE DRAWINGS

In order to more fully describe embodiments of the present invention, reference is made to the accompanying drawings. These drawings are not to be considered limitations in the scope of the invention, but are merely illustrative.

DETAILED DESCRIPTION OF SPECIFIC EMBODIMENTS

The description above and below and the drawings of the present document focus on one or more currently preferred embodiments of the present invention and also describe some exemplary optional features and/or alternative embodiments. The description and drawings are for the purpose of illustration and not limitation. Those of ordinary skill in the art would recognize variations, modifications, and alternatives. Such variations, modifications, and alternatives are also within the scope of the present invention. Section titles are terse and are for convenience only.

Figure 1:
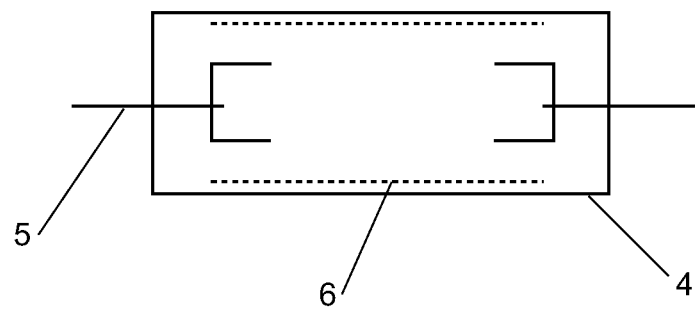
FIG. 1 is an illustration of prior art UV lamps.
Figure 2:
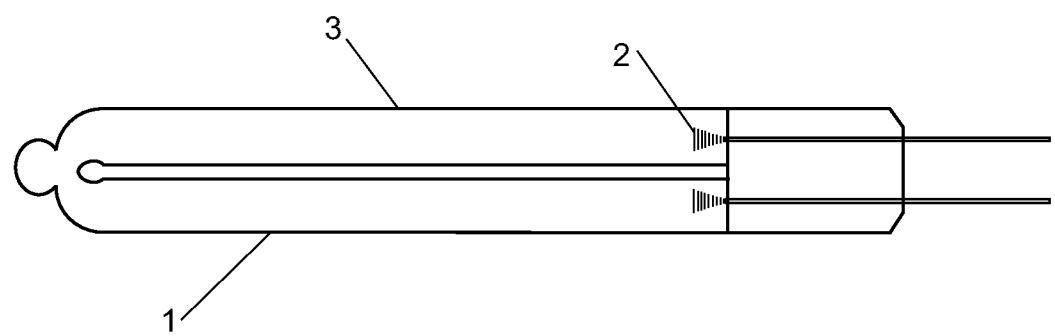
FIG. 2 Illustrates a UV lamp in accordance with an embodiment of the present invention.
Figure 3:
FIG. 3 illustrates a conical electrode of the UV lamp in accordance with an embodiment of the present invention.

As shown in FIG. 1 and FIG. 2, according to an embodiment of the present invention, the lamp is a "U" shaped UV lamp having a first end and a second end, the lamp comprises a glass shell 1 and an electrode 2 positioned on each of the first end and second end of the lamp. The electrode 2 is a conically shaped coiled wire, in which the inner and bottom portion of the cone is hollow. In an embodiment of the present invention, there is an ozone resistant layer 3 coated on the outer surface of the lamp for controlling the ozone concentration created by the lighting of the lamp.

The lamp is about 2.5~5 mm in diameter with a shell 1 made of high quality deoxy-quartz glass tube or like material to ensure the discharge ability of the gas (for example, Mercury gas or a blending of Neon and Argon) inside the tube lasts longer and is more stable. The shape of the tube is long and thin, allowing the working voltage to be high while the current is low; this decreases the energy consumption of the electrode 2 and the self-absorption rate of the electric particles during gas discharge, thereby further increasing the efficiency of the lamp.

The lamp is based on cold-cathode and hot-emission theory. The electrode 2 on each end of the lamp is made of tungsten filament and coiled in a cone shape. This structure reduces the thermal capacity of the electrode 2, allows the lamp to start more quickly, and decreases the emission loss of the electrode 2 when the glow discharge is transformed to an arc discharge. Furthermore, the surface area of the coiled electrode 2 is as 1.57 times (the sides surface area of a round wire is $\pi$ times of its diameter, so one side is $\pi/2$=1.57) that of a common electrode (such as in neon lights). The electrode 2 is a coiled wire in a conical shape. Thus, the electron beam is emitted in a gradually opening linear shape. Unlike common UV lamps, the emission loading is changed from a point emission to a surface emission, thus decreasing the electron scattering and allowing the lamp to resist the fierce impact from positive ions. The whole shape and structure of the electrode 2 improves the brightness and extends the life of the lamp.

In theory, the life span of the common cold cathode UV lamp is about 20,000 hours, but is much shorter in practice. In contrast, the life span of the lamp of the present invention is about 60,000 hours. The present invention can also be provided in shapes other than the "U"-shaped such as a straight tube or in an annular shape.

The lamp according to an embodiment of the present invention can radiate various UV rays with wavelengths of 185 nm, 253.7 nm, 297 nm, 313 nm and 365 nm, and also when it is not coated with fluorescent powder on the inside surface of the lamp. The lamp has anti-bactericidal properties and can also decompose organisms such that it can be used in the health care and environment protection industries. In an embodiment of the present invention, the outer surface of the lamp is coated with an ozone resistant layer 3 of nano-material such as nano-$TiO_2$; the coating 3 works to increase the effect of photocatalysis, and to control the ozone concentration created by the lighting of the lamp. This improves the efficiency of photocatalysis of the UV lamp and its sterilizing effect and can also improve the practicability of this UV lamp in the photocatalysis field.

Throughout the description and drawings, example embodiments are given with reference to specific configurations. It will be appreciated by those of ordinary skill in the art that the present invention can be embodied in other specific forms. Those of ordinary skill in the art would be able to practice such other embodiments without undue experimentation. The scope of the present invention, for the purpose of the present patent document, is not limited merely to the specific example embodiments of the foregoing description, but rather is indicated by the appended claims. All changes that come within the meaning and range of equivalents within the claims are intended to be considered as being embraced within the spirit and scope of the claims.

What is claimed is:

1. An ultraviolet lamp having one or more ends, the lamp comprising a shell, and one or more cold cathode electrodes, at least one electrode set on each of the one or more ends of the lamp, wherein each of said one or more electrodes comprises a coiled wire wherein the wire coils around an outer surface circumference forming a shape of a hollow cone.

2. The ultraviolet lamp as in claim 1, wherein each electrode has a top and a bottom, the top having a circumference of the coiled wire larger than a circumference of the coiled wire of the bottom and, wherein an inner portion and the bottom of each of the electrodes are hollow.

3. The ultraviolet lamp as in claim 1, wherein said lamp is "U" shaped.

4. The ultraviolet lamp as in claim 1, wherein said lamp is annular shaped.

5. The ultraviolet lamp as in claim 1, wherein an ozone resistant layer is coated on an outer surface of the lamp shell.

6. The ultraviolet lamp as in claim 5, wherein the ozone resistant layer includes nano-$TiO_2$.

7. The ultraviolet lamp according to claim 1, wherein the lamp emits UV rays having wavelengths from about 185 nm to about 365 nm, without a fluorescent coating on an inside surface of the lamp.

8. The ultraviolet lamp according to claim 1, wherein the shell comprises a deoxy-quartz glass tube.

9. An ultraviolet lamp, comprising:
a first end and a second end;
a shell; and
a cold cathode electrode positioned on both ends of the lamp, wherein each electrode comprises a coiled wire wherein the wire coils around an outer surface circumference forming a shape of a hollow cone; and
wherein an electron beam is emitted in a gradually opening linear shape and an emission loading is evenly distributed on the emission surface of each electrode wire, thus minimizing electron scattering and allowing the lamp to resist a strong impact from positive ions.

10. The ultraviolet lamp as in claim 9, wherein each electrode has a top and a bottom, the top having a circumference of the coiled wire larger than a circumference of the coiled wire of the bottom and, wherein an inner portion and the bottom of each electrode are hollow.

11. The ultraviolet lamp as in claim 9, wherein said lamp is "U" shaped.

12. The ultraviolet lamp as in claim 9, wherein an ozone resistant layer is coated on an outer surface of the lamp shell.

13. The ultraviolet lamp as in claim 12, wherein the ozone resistant layer includes nano-$TiO_2$.

14. An ultraviolet lamp, comprising:
a first end and a second end;
a shell having an ozone resistant outer layer, and
a cold cathode electrode positioned on each end of the lamp, wherein each electrode comprises a coiled wire wherein the wire coils around an outer surface circumference which forms a shape of a hollow cone; and
wherein an electron beam is emitted in a gradually opening linear shape and an emission loading is evenly distributed on the emission surface of each electrode wire, thus minimizing electron scattering and allowing the lamp to resist a fierce impact from positive ions.

15. The ultraviolet lamp as in claim 14, wherein each electrode has a top and a bottom, the top having a circumference of the coiled wire larger than a circumference of the coiled wire of the bottom and, wherein an inner portion and the bottom of each electrode are hollow.

16. The ultraviolet lamp as in claim 14, wherein said lamp is "U" shaped.

17. The ultraviolet lamp according to claim 14, wherein the lamp emits UV rays having wavelengths from 185 nm-365 nm, without a fluorescent coating on an inside surface of the lamp.

18. The ultraviolet lamp as in claim 14, wherein the ozone resistant layer includes nano-$TiO_2$.

* * * * *